(12) United States Patent
Touge et al.

(10) Patent No.: US 8,404,879 B2
(45) Date of Patent: Mar. 26, 2013

(54) RUTHENIUM-DIAMINE COMPLEX AND METHODS FOR PRODUCING OPTICALLY ACTIVE COMPOUNDS

(75) Inventors: Taichiro Touge, Hiratsuka (JP); Hideki Nara, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 20 days.

(21) Appl. No.: 12/835,626

(22) Filed: Jul. 13, 2010

(65) Prior Publication Data

US 2011/0009646 A1    Jan. 13, 2011

(30) Foreign Application Priority Data

Jul. 13, 2009 (JP) ................................. 2009-164712

(51) Int. Cl.
*C07F 15/00*   (2006.01)
*C07F 17/02*   (2006.01)
*C07F 7/18*    (2006.01)
*C07F 7/08*    (2006.01)

(52) U.S. Cl. ............... 556/136; 556/137; 556/9; 556/12
(58) Field of Classification Search .......................... None
See application file for complete search history.

(56) References Cited

U.S. PATENT DOCUMENTS

| | | | | |
|---|---|---|---|---|
| 6,156,692 A | * | 12/2000 | Nubel et al. | 502/155 |
| 6,372,931 B1 | * | 4/2002 | Blacker et al. | 556/136 |
| 6,544,923 B1 | * | 4/2003 | Huang et al. | 502/159 |
| 7,250,526 B2 | * | 7/2007 | Blacker et al. | 556/136 |
| 7,754,889 B2 | * | 7/2010 | Amano et al. | 548/101 |
| 7,880,025 B2 | * | 2/2011 | Touge et al. | 556/12 |
| 2005/0101787 A1 | * | 5/2005 | Watanabe et al. | 548/495 |
| 2010/0261924 A1 | * | 10/2010 | Watanabe et al. | 556/137 |
| 2010/0298588 A1 | * | 11/2010 | Touge et al. | 556/12 |

FOREIGN PATENT DOCUMENTS

WO    0114060 A2    3/2001

OTHER PUBLICATIONS

Extended European Search Report dated Sep. 13, 2010, corresponding to Patent Application No. EP 10 00 7168.
"Asymmetric Transfer Hydrogenation of Imines", Uematsu N., et al., Journal of the American Chemical Society, vol. 1996, pp. 4916-4917.

* cited by examiner

*Primary Examiner* — Porfirio Nazario Gonzalez
*Assistant Examiner* — James Meadows
(74) *Attorney, Agent, or Firm* — Edwards Wildman Palmer LLP; Peter F. Corless

(57) ABSTRACT

There are provided a ruthenium-diamine complex, and methods for selectively producing an optically active alcohol and an optically active amine, which are important as precursors for the synthesis of medicinal drugs and functional materials, using the ruthenium-diamine complex as a catalyst. The invention provides a ruthenium-diamine complex prepared by introducing a trisubstituted silyl group into an aromatic compound (arene) moiety that is coordinated with a ruthenium complex having an optically active diamine as a ligand, a catalyst for asymmetric reduction formed from the ruthenium-diamine complex, and a method for producing an optically active alcohol or an optically active amine using the catalyst.

6 Claims, No Drawings

RUTHENIUM-DIAMINE COMPLEX AND METHODS FOR PRODUCING OPTICALLY ACTIVE COMPOUNDS

CROSS-REFERENCES TO RELATED APPLICATIONS

This application claims under 35 U.S.C. §119(a) the benefit of Japanese Application No. 2009-164712 filed Jul. 13, 2009 the entire contents of which is incorporated herein by reference.

TECHNICAL FIELD

The present invention relates to a novel ruthenium-diamine complex, and methods for selectively producing an optically active alcohol and an optically active amine, which are important as precursors for the synthesis of medicinal drugs and functional materials, using the ruthenium-diamine complex as a catalyst.

BACKGROUND ART

A number of asymmetric reactions, including asymmetric reduction, have been developed, and various asymmetric metal complexes having optically active phosphine ligands as the catalyst that are used in these reactions, have been also reported. Among them, transition metal complexes, such as ruthenium, rhodium and iridium, coordinated with optically active nitrogen compounds, have excellent performance as catalysts for asymmetric synthesis reactions.

Thus, a number of various optically active nitrogen compounds have been developed heretofore, in order to enhance the performance of these catalysts (see Chem. Rev. (1992) p. 1051; J. Am. Chem. Soc. 117 (1995) p. 7562; J. Am. Chem. Soc. 118 (1996) p. 2521; J. Am. Chem. Soc. 118 (1996) p. 4916; and the like).

DISCLOSURE OF THE INVENTION

Problems to be Solved by the Invention

However, in the conventional methods making use of these complexes, the target reaction or a reaction substrate thereof may lead to unsatisfactory catalyst activity and asymmetric yield. Thus, development of new complexes is strongly desired.

Means for Solving the Problems

The inventors of the present invention conducted an investigation to solve the problems described above, and found a novel ruthenium-diamine complex prepared by introducing a trisubstituted silyl group into an arene moiety that is coordinated with a ruthenium complex having an optically active diamine.

The present invention includes the following items.
[1] A ruthenium complex represented by the following formula (1):

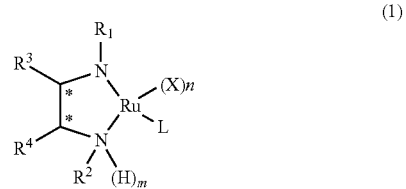

wherein * represents an asymmetric carbon atom;
$R^1$ represents an alkyl group having 1 to 10 carbon atoms; an alkanesulfonyl group having 1 to 10 carbon atoms which may be substituted with a halogen atom; an arenesulfonyl group which may be substituted with an alkyl group having 1 to 10 carbon atoms, a halogenated alkyl group having 1 to 10 carbon atoms or a halogen atom; an alkoxycarbonyl group having 2 to 11 carbon atoms; or a benzoyl group which may be substituted with an alkyl group having 1 to 10 carbon atoms;
$R^2$ represents a hydrogen atom or an alkyl group having 1 to 10 carbon atoms;
X represents a trifluoromethanesulfonyloxy group, a p-toluenesulfonyloxy group, a methanesulfonyloxy group, a benzenesulfonyloxy group, a hydrogen atom, or a halogen atom;
m and n each represents 0 or 1, in addition m+n is 0 or 2;
$R^3$ and $R^4$ each independently represents an alkyl group having 1 to 10 carbon atoms; a phenyl group which may be substituted with an alkyl group having 1 to 10 carbon atoms, an alkoxy group having 1 to 10 carbon atoms or a halogen atom; or a cycloalkyl group having 3 to 8 carbon atoms, or $R^3$ and $R^4$ may be joined to form a ring; and
L represents an aromatic compound represented by the following formula (2):

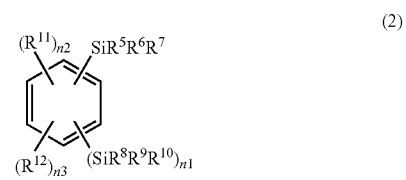

wherein $R^5$, $R^6$, $R^7$, $R^8$, $R^9$ and $R^{10}$ each independently represents an alkyl group having 1 to 10 carbon atoms; a cycloalkyl group having 3 to 6 carbon atoms; or a phenyl group which may be substituted with an alkyl group having 1 to 10 carbon atoms or an alkoxy group having 1 to 10 carbon atoms;
$R^{11}$ and $R^{12}$ each independently represents a hydrogen atom, an alkyl group having 1 to 10 carbon atoms, or an alkoxy group having 1 to 10 carbon atoms; and
n1, n2 and n3 each represents 0 or 1.
[2] A method for producing an optically active alcohol, comprising reducing the carbonyl group of a carbonyl compound in the presence of the ruthenium complex according to the above [1] and a hydrogen donor.
[3] A method for producing an optically active amine, comprising reducing the imino group of an imine compound in the presence of the ruthenium complex according to the above [1] and a hydrogen donor.

[4] The method for producing according to the above [2] or [3], wherein the hydrogen donor is selected from formic acid, a formic acid alkali metal salt, and an alcohol having a hydrogen atom on the α-position of the carbon atoms substituted with a hydroxyl group.

[5] A catalyst for asymmetric reduction comprising the ruthenium complex according to the above [1].

Effects of the Invention

The present invention is to provide a novel ruthenium-diamine complex having a trisubstituted silyl group introduced to the arene moiety coordinated with ruthenium. The ruthenium-diamine complex of the present invention has a strong catalytic activity, and is useful with various hydrogenation catalysts. In addition, the ruthenium-diamine complex of the invention is excellent in steric selectivity and gives a high asymmetric yield.

When the ruthenium-diamine complex of the invention is used, an optically active alcohol or an optically active amine, which is useful as a raw material or the like for the production of medicinal drugs and functional materials, can be selectively produced.

MODES FOR CARRYING OUT THE INVENTION

In the formula (1) of the present invention, the alkyl group having 1 to 10 carbon atoms represented by $R^1$ and $R^2$ may be a linear or branched alkyl group. Specific examples of the alkyl group include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an n-nonyl group, an n-decyl group, and the like.

In the formula (1) of the present invention, the alkanesulfonyl group having 1 to 10 carbon atoms which may be substituted with a halogen atom, as represented by $R^1$, may be, for example, an alkanesulfonyl group such as a methanesulfonyl group, an ethanesulfonyl group, a 1-propanesulfonyl group, a 2-propanesulfonyl group, a 1-butanesulfonyl group, or a 1-hexanesulfonyl group; or a perfluoroalkyl group such as a trifluoromethanesulfonyl group, a pentafluoroethanesulfonyl group or a heptafluoropropanesulfonyl group.

In the formula (1) of the present invention, the arene of the arenesulfonyl group represented by $R^1$ may be a phenyl group, a naphthyl group or the like, and substituents that may be substituted on these arene groups include an alkyl group having 1 to 10 carbon atoms such as described above, a perfluoroalkyl group, and a halogen atom such as a fluorine atom or a chlorine atom. Specific examples of the arenesulfonyl group include a benzenesulfonyl group, o-, m- and p-toluenesulfonyl groups, o-, m- and p-ethylbenzenesulfonyl groups, o-, m- and p-isopropylbenzenesulfonyl groups, o-, m- and p-t-butylbenzenesulfonyl groups, a 2,4,6-trimethylbenzenesulfonyl group, a 2,4,6-triisopropylbenzenesulfonyl group, o-, m- and p-trifluoromethylbenzenesulfonyl groups, o-, m- and p-fluorobenzenesulfonyl groups, o-, m- and p-chlorobenzenesulfnoyl groups, a pentafluorobenzenesulfonyl group, and the like.

In the formula (1) of the present invention, the alkoxycarbonyl group having 2 to 11 carbon atoms represented by $R^1$ may be, for example, a methoxycarbonyl group, an ethoxycarbonyl group, an isopropyloxycarbonyl group, a t-butoxycarbonyl group, or the like. Furthermore, the benzoyl group which may be substituted with an alkyl group having 1 to 10 carbon atoms may be, for example, a benzoyl group, o-, m- and p-toluoyl groups, o-, m- and p-ethylbenzoyl groups, o-, m- and p-t-butylbenzoyl groups, and the like.

In the formula (1) of the present invention, the alkyl group having 1 to 10 carbon atoms represented by $R^3$ and $R^4$ may be a linear or branched alkyl group. Specific examples of the alkyl group include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an n-nonyl group, an n-decyl group, and the like.

In the formula (1) of the present invention, examples of the alkyl group of the phenyl group which may be substituted with an alkyl group having 1 to 10 carbon atoms, an alkoxy group having 1 to 10 carbon atoms or a halogen atom, as represented by $R^3$ and $R^4$, include those groups mentioned above. Examples of the halogen atom include a fluorine atom, a chlorine atom and a bromine atom.

The alkoxy group having 1 to 10 carbon atoms may be a linear or branched alkoxy group, and specific examples of the alkoxy group include a methoxy group, an ethoxy group, an n-propoxy group, an isopropoxy group, an n-butoxy group, an isobutoxy group, an s-butoxy group, a t-butoxy group, an n-pentyloxy group, an n-hexyloxy group, an n-heptyloxy group, an n-octyloxy group, an n-nonyloxy group, an n-decyloxy group, and the like.

In the formula (1) of the present invention, the cycloalkyl group having 3 to 8 carbon atoms represented by $R^3$ and $R^4$ may be a cyclopropyl group, a cyclobutyl group, a cyclopentyl group, a cyclohexyl group, a cycloheptyl group, or a cyclooctyl group, and these cycloalkyl groups may be each substituted with an alkyl group such as a methyl group, an isopropyl group or a t-butyl group.

When $R^3$ and $R^4$ are joined to form a ring, $R^3$ and $R^4$ together form a linear or branched alkylene group having 2 to 10 carbon atoms, and preferably 3 to 10 carbon atoms, and this alkylene group forms, together with adjacent carbon atoms, a 4- to 8-membered, and preferably a 5- to 8-membered, cycloalkane ring. Preferred examples of the cycloalkane ring include a cyclopentane ring, a cyclohexane ring and a cycloheptane ring, and these rings may be each substituted with an alkyl group such as a methyl group, an isopropyl group or a t-butyl group, as a substituent.

In regard to L represented by the formula (1) according to the present invention, examples of the alkyl group having 1 to 10 carbon atoms and the alkoxy group having 1 to 10 carbon atoms, which are represented by $R^5$, $R^6$, $R^7$, $R^8$, $R^9$, $R^{10}$, $R^{11}$ and $R^{12}$ in the formula (2), include those groups described above, and examples of the cycloalkyl group having 3 to 6 carbon atoms represented by $R^5$ to $R^{10}$ include a cyclopropyl group, a cyclobutyl group, a cyclopentyl group, and a cyclohexyl group.

Preferred examples of the compound represented by the formula (2) include benzene which may be substituted with an alkyl, and is substituted with a tri(saturated hydrocarbyl) substituted silyl group, such as trimethylsilylbenzene, trimethylsilyltoluene, trimethylsilylxylene, triethylsilylbenzene, triethylsilyltoluene, triethylsilylxylene, triisopropylsilylbenzene, triisopropylsilyltoluene, triisopropylsilylxylene, t-butyldimethylsilylbenzene, t-butyldimethylsilyltoluene, or t-butyldimethylsilylxylene; a tri(unsaturated or saturated hydrocarbyl) substituted silyl group, such as triphenylsilylbenzene, triphenylsilyltoluene, triphenylsilylxylene, dimethylphenylsilylbenzene, dimethylphenylsilyltoluene, or dimethylphenylsilylxylene; or a tri(alkoxy) substituted alkoxysilyl group, such as trimethoxysilylbenzene, trimethoxysilyltoluene, trimethoxysilylxylene, triethoxysilylbenzene, triethoxysilyltoluene, or triethoxysilylxylene; and the like.

The method for producing a ruthenium complex of the present invention is, for example, represented by the following scheme, as described in J. Am. Chem. Soc., 1995, 117, p. 7562 or Angew. Chem. Int. Ed. Engl., 1997, 36, p. 285.

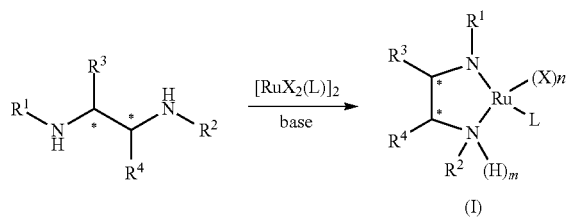

(wherein the symbols in the scheme have the same definitions as described above.)

The reaction between the optically active diamine compound and the ruthenium compound is theoretically an equimolar reaction, it is preferable to use the optically active diamine compound in an equimolar amount or more with respect to the ruthenium compound, from the viewpoint of the rate of catalyst preparation.

Furthermore, in the case of a ruthenium complex of the formula (1) in which m=n=1 and X is a halogen atom, it is preferable to incorporate a base into the reaction system at the time of catalyst preparation. The base in this case is preferably tertiary organic amines such as trimethylamine, triethylamine or triisopropylamine, and particularly preferably triethylamine. The amount of addition of the base is an equimolar amount or more with respect to the ruthenium atom. The solvent used in this case is not particularly limited, but ethers such as diethyl ether and tetrahydrofuran; alcohols such as methanol, ethanol and isopropanol; aromatic hydrocarbons such as toluene and xylene; halogenated hydrocarbons such as dichloromethane, 1,2-dichloroethane and chloroform; aprotic polar solvents such as acetonitrile and N,N-dimethylformamide; and the like are preferred, while isopropanol being particularly preferred.

The ruthenium complex having a halogen atom for X, which is obtained by the method described above, may be easily converted to a ruthenium complex having a hydrogen atom for X, by contacting the complex with a hydrogen donor. As for the hydrogen donor, those compounds generally used as hydrogen donors in hydrogen transfer type reduction reactions, for example, metal hydrides such as borohydride compounds, hydrogen gas, formic acid and isopropanol, are similarly used. The amount of use of the hydrogen donor may be preferably an equimolar amount or more with respect to the catalyst in terms of hydride.

Furthermore, examples of the base used to achieve basic conditions include tertiary organic amines such as trimethylamine, triethylamine and triisopropylamine; inorganic bases such as LiOH, NaOH, KOH and $K_2CO_3$; and metal alkoxides such as sodium methoxide and potassium methoxide. The conversion of X from a halogen atom to a hydrogen atom in the ruthenium complex of the present invention, may be preliminarily carried out before the ruthenium complex is supplied to the asymmetric reduction reaction, or may be carried out within the asymmetric reduction reaction system (in situ method).

In the preparation of a ruthenium complex of the formula (1) in which m=n=0, examples of the solvent that may be preferably used include ethers such as diethyl ether and tetrahydrofuran; aromatic hydrocarbons such as toluene and xylene; and halogen solvents such as methylene chloride, and among them, toluene and methylene chloride are preferred. Examples of the base that may be used include inorganic bases such as LiOH, NaOH, KOH and $K_2CO_3$; and metal alkoxides such as sodium methoxide and potassium methoxide, and among them, KOH and NaOH are particularly preferred.

Preparation of the ruthenium complex of the present invention is usually carried out at 100° C. or below, and preferably at 80° C. or below.

After completion of the reaction, the desired ruthenium complex may be separated by concentration of the reaction mixture or addition of a poor solvent or general standard crystallization techniques. Furthermore, when a hydrogen halide salt is side-produced during the preparation of the ruthenium complex, an operation of washing with water may also be carried out as necessary.

Furthermore, in the case of simultaneously carrying out the catalyst preparation within the asymmetric reduction reaction system (in situ method), use may be made of a method of contacting the ruthenium compound with the optically active diamine compound in the co-presence of a hydrogen donor, and then adding a reduction substrate; or a method of simultaneously adding the ruthenium compound, the optically active diamine compound and a reduction substrate. In both of these cases, the ratio of amount of use of the ruthenium compound and the optically active diamine compound, or the like is as described above. Furthermore, it is preferable to set up the reaction conditions such as reaction solvent and temperature according to the asymmetric reduction reaction conditions that will be described later.

The ruthenium-arene complex $[RuX_2(L)]_2$, which is a raw material of the ruthenium complex of the present invention, may be produced as follows. For example, a 1,3-diene such as isoprene and an acetylene derivative having a silicon atom such as trimethylsilylacetylene are subjected to the Diels-Alder reaction using a metal catalyst such as cobalt, according to the methods described in, for example, Tetrahedron Letters 41 (2000) p. 6757 and Synthesis (2002) p. 609, and thereby a 1,4-cyclohexadiene derivative is synthesized. Subsequently, the 1,4-cyclohexadiene derivative obtained as described above is reacted with ruthenium chloride trihydrate in an alcohol solvent such as 2-methoxyethanol in the presence of a base such as $NaHCO_3$, as described in, for example, J. Chem. Soc., Dalton Trans (1974) p. 233 and Organic & Biomolecular Chemistry (2007) p. 1093, and thereby the intended ruthenium-arene complex may be synthesized. The present production method is preferably carried out in the presence of an inactive gas such as nitrogen gas or argon gas.

The asymmetric reduction reaction of the present invention is carried out by reacting the ruthenium complex represented by the formula (1) with a carbonyl compound or imines in the co-presence of a hydrogen donor. The hydrogen donor is not particularly limited if it is a compound generally used in hydrogen transfer type reduction reactions, such as formic acid or a salt thereof, or isopropanol which is an alcohol having a hydrogen atom at the α-position of the carbon atom substituted with a hydroxyl group. Furthermore, hydrogen gas may also be used as the hydrogen donor. It is preferable that the asymmetric reduction reaction is carried out in the presence of a base. Examples of the base include tertiary organic amines such as trimethylamine, triethylamine, and triisopropylamine; and inorganic bases such as LiOH, NaOH, KOH and $K_2CO_3$. A suitable base is triethylamine. The base is used in an excess with respect to the ruthenium complex, for example, in a 1- to 10000-fold molar amount. In the case of using triethylamine, it is preferable to use the catalyst in a 1- to 1000-fold amount.

Among combinations of the hydrogen donor and a base, when the hydrogen donor is formic acid, it is preferable to use an amine as a base. In this case, formic acid and the amine may be added separately into the reaction system, or it is also acceptable to prepare an azeotropic mixture of formic acid and the amine in advance and to use the mixture.

In regard to the reaction, usually, if the hydrogen donor is a liquid, the hydrogen donor may be used as the reaction solvent, or in order to dissolve the raw material, non-hydrogen-donating solvents such as toluene, tetrahydrofuran, acetonitrile, dimethylformamide, dimethylsulfoxide, acetone and dichloromethane may be used singly or in mixture, as a co-solvent. When hydrogen gas is used, use of alcohol solvent such as methanol, ethanol and isopropanol, is preferred.

The amount of use of the ruthenium complex as a catalyst is selected such that the molar ratio of the substrate (carbonyl compound or imines) (S) to the ruthenium metal atom (C) (S/C) is in the range of 10 to 1000000, and preferably in the range of 100 to 5000.

In regard to the amount of the hydrogen donor with respect to the carbonyl compound or imines, an equimolar amount or more is usually used. Particularly, when the hydrogen donor is formic acid or a salt thereof, the amount is preferably a 1.5-fold molar amount or more, while an amount of 20-fold molar amount or less, and preferably a 10-fold molar amount or less, is used. On the other hand, when the hydrogen donor is isopropanol or the like, the hydrogen donor is used in a large excess with respect to the substrate from the viewpoint of reaction equilibrium, and is usually used in a 1000-fold molar amount or less.

The reaction temperature is selected in the range of $-70$ to $100°$ C., and preferably 0 to $70°$ C.

The reaction pressure is not particularly limited, and the reaction is usually carried out at 0.5 to 2 atmospheres, and preferably under normal pressure. When hydrogen gas is used, the reaction pressure is usually carried out at 5 MPa or less, and preferably at 3 MPa or less.

The reaction time is 1 to 100 hours, and usually 2 to 50 hours.

After the reaction, the produced optically active product can be separated and purified by common operations such as distillation, extraction, chromatography and reprecipitation.

EXAMPLES

Hereinafter, the present invention will be described in detail by way of Examples, but the present invention is not intended to be limited thereto.

The NMR spectra used in the identification of the complex and purity determination in the following Examples and Reference Examples, were measured with a Mercury Plus 300 4N spectrometer manufactured by Varian Technology Japan, Ltd. The GC analysis of reaction was measured using Chirasil-DEX CB (0.25 mm×25 m, 0.25 μm) (manufactured by Varian, Inc.)

The symbols used in the Examples represent the following meanings.
TMS-toluene: 4-(trimethylsilyl)toluene
TIPS-toluene: 4-(triisopropylsilyl)toluene
Msdpen: N-methanesulfonyl-1,2-diphenylethylenediamine
Tsdpen: N-(p-toluenesulfonyl)-1,2-diphenylethylenediamine However, the diamine in the complex represents a diamine from which one or two hydrogen atoms have been eliminated.

Example 1

Synthesis of RuCl{(R,R)-Msdpen}(TMS-toluene)

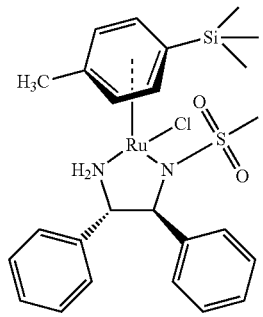

In a 50-ml Schlenck tube, 0.385 g (0.574 mmol) of [RuCl$_2$(TMS-toluene)]$_2$, 0.333 g (1.15 mmol) of (R,R)-Msdpen, and 0.32 ml (2.3 mmol) of triethylamine were dissolved in 10 ml of isopropanol, and the solution was stirred for 1.5 hours at $80°$ C. Subsequently, isopropanol was evaporated under reduced pressure until the volume of isopropanol reached approximately a half the original volume. 20 ml of distilled water was added thereto, and crystals precipitated therefrom were filtered. The filter cake was washed with water. The obtained crystals were dried under reduced pressure at $60°$ C. for 5 hours, and thereby 0.60 g of the desired complex, RuCl[(R,R)-Msdpen] (TMS-toluene) was obtained at a yield of 89%.

$^1$H-NMR (CDCl$_3$, 300 MHz) δ:
0.45 (s, 9H, —Si(CH$_3$)$_3$),
2.37 (s, 3H, CH$_3$—C$_6$H$_4$—Si(CH$_3$)$_3$).
2.47 (s, 3H, —SO$_2$—CH$_3$), 3.72 (m, 1H, NHH), 3.72 (m, 1H, HCNMs),
3.90 (m, 1H, HCNH$_2$), 5.10 (m, 1H, NHH),
5.36, 5.44, 5.71, 5.80 (each d, 1H, CHarene in TMS-toluene),
6.84-7.13 (10H, phenyl proton of diphenylethylenediamine)

Example 2

Synthesis of RuCl[(R,R)-Tsdpen](TMS-toluene)

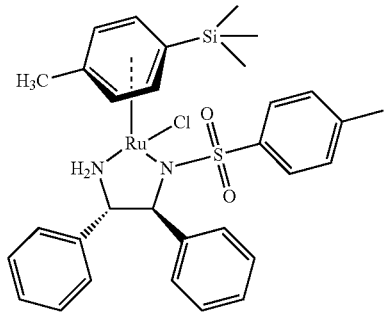

In a 50-ml Schlenk tube, 0.46 g (0.682 mmol) of [RuCl$_2$(TMS-toluene)]$_2$, 0.5 g (1.36 mmol) of (R,R)-Tsdpen, and 0.38 ml (2.7 mmol) of triethylamine were dissolved in 13 ml of isopropanol, and the solution was stirred for one hour at 80° C. Subsequently, isopropanol was evaporated under reduced pressure until the volume of isopropanol reached approximately a half the original volume. 25 ml of distilled water was added thereto, and crystals precipitated therefrom were filtered. The filter cake was washed with water. The obtained crystals were dried under reduced pressure at 60° C. for 5 hours, and thereby 0.82 g of the desired complex, RuCl [(R,R)-Tsdpen] (TMS-toluene) was obtained at a yield of 90%.

$^1$H-NMR (CD$_2$Cl$_2$, 300 MHz) δ:
0.47 (s, 9H, Si(CH$_3$)$_3$), 2.26 (s, 3H, —SiC$_6$H$_4$—CH$_3$),
2.42 (s, 3H, —SO$_2$C$_6$H$_4$—CH$_3$), 3.67 (m, 1H, NHH),
3.67 (m, 1H, HCNH$_2$), 3.85 (m, 1H, HCN-pTs), 5.05 (m, 1H, NHH),
5.48, 5.58, 5.67, 5.79 (each d, 1H; CHarene in TMS-toluene),
6.63-7.16 (14H, tosyl group of Tsdpen moiety and proton of phenyl group)

Example 3

Hydrogen Transfer Type Reaction of 1-acetylnaphthalene

In a 20-ml Schlenk tube, 28 mg (0.05 mmol) of RuCl[(R,R)-Msdpen] (TMS-toluene) (S/C=100), 0.85 g (5.0 mmol) of 1-acetylnaphthalene, and 2.5 ml of a formic acid-triethylamine (5:2) azeotropic mixture were mixed, and the tube was purged with nitrogen. The mixture was allowed to react for 48 hours at 30° C. The yield and optical purity were measured by GC analysis, and as a result, optically active 1-naphthylethanol, which was the target reduction product, was obtained at a conversion rate of 83.6% and an optical purity of 96.2% ee.

Example 4

Hydrogen Transfer Type Reaction of (E)-1-phenyl-N-(1-phenylethylidene)methanamine In a 20-ml Schlenk tube, 28 mg (0.05 mmol) of RuCl((R,R)-Msdpen) (p-TMS-toluene) (S/C=100), 1.04 g (5 mmol) of the title imine, 10 ml of dichloromethane, and 2.5 ml of a formic acid-triethylamine (5:2) azeotropic mixture were mixed, and the mixture was allowed to react for 24 hours at 30° C. The yield and optical purity were measured by GC analysis, and as a result, optically active N-benzyl-1-phenethylamine, which was the target amine, was obtained at a yield of 86% and an optical purity of 76% ee.

Reference Example 1

Synthesis of [RuCl$_2$(TMS-toluene)]$_2$

In a 50-ml Schlenk tube, 2.13 g (9.0 mmol) of ruthenium chloride trihydrate, 6.8 g (40.8 mmol) of trimethyl(4-methylcyclohexa-1,4-dienyl)silane, 0.76 g (9.0 mmol) of NaHCO$_3$, and 2.3 ml of water were dissolved in 22 ml of 2-methoxyethanol, and the solution was allowed to react for one hour at 130° C. Subsequently, the reaction mixture was left to cool down to room temperature, and precipitated crystals were filtered. Thereby, 2.06 g of desired [RuCl$_2$(TMS-toluene)]$_2$ was obtained at a yield of 76%.

$^1$H-NMR (CDCl$_3$, 300 MHz) δ:
0.39 (s, 9H), 2.11 (s, 3H), 5.33 (d, 2H), 5.59 (d, 2H)

Reference Example 2

Synthesis of [RuCl$_2$ (TIPS-toluene)]$_2$

In a 150-ml Schlenk tube, 1.18 g (4.5 mmol) of ruthenium chloride trihydrate, 5.6 g (22.5 mmol) of triisopropyl (4-methylcyclohexa-1,4-dienyl) silane, and 0.38 g (4.5 mmol) of NaHCO$_3$ were dissolved in 11 ml of 2-methoxyethanol, and the solution was allowed to react for 9 hours at 130° C. Subsequently, the reaction mixture was allowed to cool down to room temperature, and precipitated crystals were filtered. Thereby, 1.4 g of desired [RuCl$_2$(4-(triisopropylsilyl)toluene)]$_2$ was obtained at a yield of 73.0%.

The triisopropylsilyl form shown in the Reference Example 2 can be used in the same manner as the trimethylsilyl form is used in the Examples described above.

$^1$H-NMR (CDCl$_3$, 300 MHz) δ:
1.15 (d, 18H), 1.42 (m, 3H), 2.09 (s, 3H), 5.34 (d, 2H), 5.64 (d, 2H)

Example 5

Synthesis of RuCl[(R,R)-Tsdpen] (TIPS-toluene)

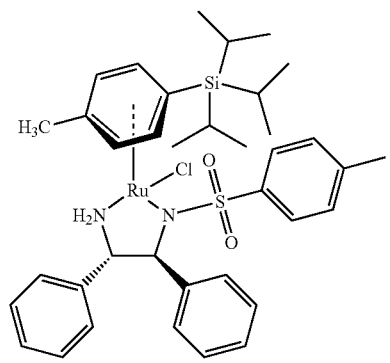

In a 50-ml Schlenk tube, 200 mg (0.238 mmol) of [RuCl$_2$ (TIPS-toluene)]$_2$, 175 mg (0.477 mmol) of (R,R)-Tsdpen, and 0.20 ml (1.4 mmol) of triethylamine were dissolved in 4 ml of isopropanol, and the solution was stirred for one hour at 80° C. Subsequently, isopropanol was evaporated under reduced pressure until the volume of isopropanol reached approximately a half the original volume. 10 ml of distilled water was added thereto, and crystals precipitated therefrom were filtered. The filter cake was washed with water. The obtained crystals were dried under reduced pressure at 60° C. for 5 hours, and thereby 0.32 g of the desired complex, RuCl [(R,R)-Tsdpen] (TIPS-toluene), was obtained at a yield of 90%.

$^1$H-NMR (CD$_2$Cl$_2$, 300 MHz) δ:
1.14 (d, 18H, Si (CH(CH$_3$)$_2$)$_3$).
1.41-1.46 (m, 3H, Si (CH(CH$_3$)$_2$)$_3$)
2.19 (s, 3H, —SiC$_6$H$_4$—CH$_3$).
2.36 (s, 3H, —SO$_2$C$_6$H$_4$—CH$_3$).
2.84-2.86 (m, 1H, NHH), 3.67 (m, 1H, HCNH$_2$).
3.75 (m, 1H, HCN-pTs), 4.91 (m, 1H, NHH),
5.45-5.71 (4H, CHarene in TIPS-toluene),
6.61-7.15 (14H, tosyl group of Tsdpen moiety and proton of phenyl group)

Example 6

Synthesis of Ru[(R,R)-Tsdpen] (TMS-toluene)

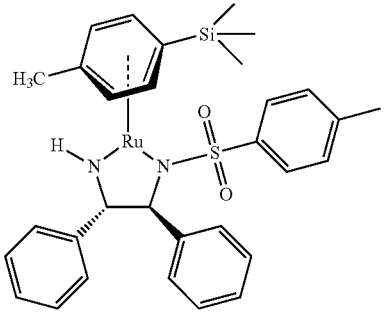

In a 25-ml Schlenk tube, 50 mg (0.075 mmol) of [RuCl$_2$(TMS-toluene)]$_2$, 54.9 mg (0.15 mmol) of (R,R)-Tsdpen, and 25 mg (0.446 mmol) of KOH were dissolved in 2 ml of dichloromethane and 2 ml of water, and the solution was stirred for 5 minutes at 30° C. The reaction mixture was separated, the dichloromethane layer was washed with water, and then the solvent was distilled off. The crystals thus obtained were dried under reduced pressure for 5 hours at 60° C., and thereby the desired complex, Ru[(R,R)-Tsdpen] (TMS-toluene), was obtained.

$^1$H-NMR (CD$_2$Cl$_2$, 300 MHz) δ:
0.20 (s, 9H, Si(CH$_3$)$_3$),
2.07 (s, 3H, —SiC$_6$H$_4$—CH$_3$).
2.12 (s, 3H, —SO$_2$C$_6$H$_4$—CH$_3$), 3.64 (1H, H—CN—H).
3.86 (1H, HCN-pTs), 5.26-5.47 (4H, CHarene in TMS-toluene),
6.60 (br, d, 1H, H—N—C)
6.45-7.17 (14H, tosyl group of Tsdpen moiety and proton of phenyl group)

Example 7

Asymmetric Hydrogenation of Acetophenone 10 mg (16.9 mmol) of RuCl [(R,R)-Msdpen] (TMS-toluene) was added into a 100-ml autoclave, and the autoclave was purged with nitrogen. Subsequently, 0.2 g (1.66 mmol) of acetophenone and 2 ml of methanol were added thereto, the pressure was increased to 3 MPa with hydrogen, and then the mixture was stirred for 19 hours at 60° C. The reaction mixture was analyzed by GC, and as a result, (R)-1-phenylethanol was found to be produced at a conversion rate of 98% and an optical purity of 80.7% ee.

Example 8

Asymmetric Hydrogenation of 4-Chromanone 7.0 mg (11.9 mmol) of RuCl[(R,R)-Msdpen] (TMS-toluene) was added into a 100-ml autoclave, and the autoclave was purged with nitrogen. Subsequently, 0.89 g (6.0 mmol) of 4-chromanone and 20 ml of methanol were added thereto, the pressure was increased to 1.5 MPa with hydrogen, and then the mixture was stirred for 23 hours at 60° C. The reaction mixture was analyzed by GC, and as a result, (R)-4-chromanol was found to be produced at a conversion rate of 84% and an optical purity of 97.0% ee.

The invention claimed is:

1. A ruthenium complex represented by the following formula (1):

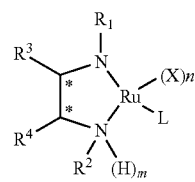

wherein * represents an asymmetric carbon atom;

R$^1$ represents an alkyl group having 1 to 10 carbon atoms; an alkanesulfonyl group having 1 to 10 carbon atoms which may be substituted with a halogen atom; an arenesulfonyl group which may be substituted with an alkyl group having 1 to 10 carbon atoms, a halogenated alkyl group having 1 to 10 carbon atoms or a halogen atom; an alkoxycarbonyl group having 2 to 11 carbon atoms; or a benzoyl group which may be substituted with an alkyl group having 1 to 10 carbon atoms;

R$^2$ represents a hydrogen atom or an alkyl group having 1 to 10 carbon atoms;

X represents a trifluoromethanesulfonyloxy group, a p-toluenesulfonyloxy group, a methanesulfonyloxy group, a benzenesulfonyloxy group, a hydrogen atom, or a halogen atom;

m and n each represent 0 or 1, in addition m+n is 0 or 2;

R$^3$ and R$^4$ each independently represent an alkyl group having 1 to 10 carbon atoms; a phenyl group which may be substituted with an alkyl group having 1 to 10 carbon atoms, an alkoxy group having 1 to 10 carbon atoms or a halogen atom; or a cycloalkyl group having 3 to 8 carbon atoms, or R$^3$ and R$^4$ may be joined to form a ring; and L represents an aromatic compound represented by the following formula (2):

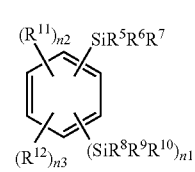

wherein R$^5$, R$^6$, R$^7$, R$^8$, R$^9$ and R$^{10}$ each independently represent an alkyl group having 1 to 10 carbon atoms; a cycloalkyl group having 3 to 6 carbon atoms; or a phenyl group which may be substituted with an alkyl group having 1 to 10 carbon atoms or an alkoxy group having 1 to 10 carbon atoms;

R$^{11}$ and R$^{12}$ each independently represent a hydrogen atom, an alkyl group having 1 to 10 carbon atoms, or an alkoxy group having 1 to 10 carbon atoms; and n1, n2 and n3 each represent 0 or 1.

2. A catalyst for asymmetric reduction comprising the ruthenium complex according to claim 1.

3. A method for producing an optically active alcohol, comprising reducing the carbonyl group of a carbonyl compound in the presence of the ruthenium complex according to claim 1 and a hydrogen donor.

4. The method for producing an optically active alcohol according to claim 3, wherein the hydrogen donor is selected from formic acid, a formic acid alkali metal salt, and an alcohol having a hydrogen atom on the α-position of the carbon atoms substituted with a hydroxyl group.

5. A method for producing an optically active amine, comprising reducing the imino group of an imine compound in the presence of the ruthenium complex according to claim 1 and a hydrogen donor.

6. The method for producing an optically active amine according to claim 5, wherein the hydrogen donor is selected from formic acid, a formic acid alkali metal salt, and an alcohol having a hydrogen atom on the α-position of the carbon atoms substituted with a hydroxyl group.

* * * * *